United States Patent

Wendt et al.

[11] Patent Number: 5,973,789
[45] Date of Patent: Oct. 26, 1999

[54] METHOD AND DEVICE FOR DETECTING SPECTRAL REFLECTANCE

[75] Inventors: Karsten Wendt, Obertshausen; Peter Schramm, Frankfurt, both of Germany

[73] Assignee: MAN Roland Druckmaschinen AG, Germany

[21] Appl. No.: 08/891,375

[22] Filed: Jul. 11, 1997

[30] Foreign Application Priority Data

Jul. 13, 1996 [DE] Germany ............................ 196 28 303

[51] Int. Cl.[6] .............................. H04N 1/12; G01N 21/55
[52] U.S. Cl. ........................... 356/447; 358/475; 356/445
[58] Field of Search ............................ 101/DIG. 45, 365;
356/445, 447; 355/51, 52; 358/475, 406

[56] References Cited

U.S. PATENT DOCUMENTS

| 3,892,492 | 7/1975 | Eichenberger | 356/447 |
| 4,711,554 | 12/1987 | Nishimori | 355/8 |
| 4,977,417 | 12/1990 | Takanashi et al. | 355/202 |

FOREIGN PATENT DOCUMENTS

| 0 378 283 B1 | 1/1990 | European Pat. Off. . |
| 34 26 188 A1 | 5/1985 | Germany . |
| 40 13 422 A1 | 10/1991 | Germany . |
| WO 95/00335 | 1/1995 | WIPO . |

*Primary Examiner*—Frank G. Font
*Assistant Examiner*—Zandra V. Smith
*Attorney, Agent, or Firm*—Leydig, Voit & Mayer, Ltd.

[57] ABSTRACT

The invention relates to a method and to a corresponding device for detecting spectral reflectance, an illuminating device arranged in a stationary fashion being used to apply to measuring fields moving relative to the measuring system radiation which differs in strength as a function of the relative speed, and the radiation reflected by the measuring fields being further processed after photoelectric conversion to derive measured variables. It is the object of the present invention to develop such a method as well as a corresponding device so that the optical reflectance-measuring system can be optimally adapted to different relative speeds given a prescribed measuring field size. This is achieved according to the invention, by controlling the light source of the illuminating device as a function of the relative speed between the measuring field and measuring system so that the spectral intensity distribution of the light source of the illuminating device is detected for the respective relative speed between the measuring fields and measuring system, and by taking into account the respectively present spectral intensity distribution of the light source of the illuminating device in processing the radiation reflected by the measuring fields to obtain measured values.

10 Claims, 7 Drawing Sheets

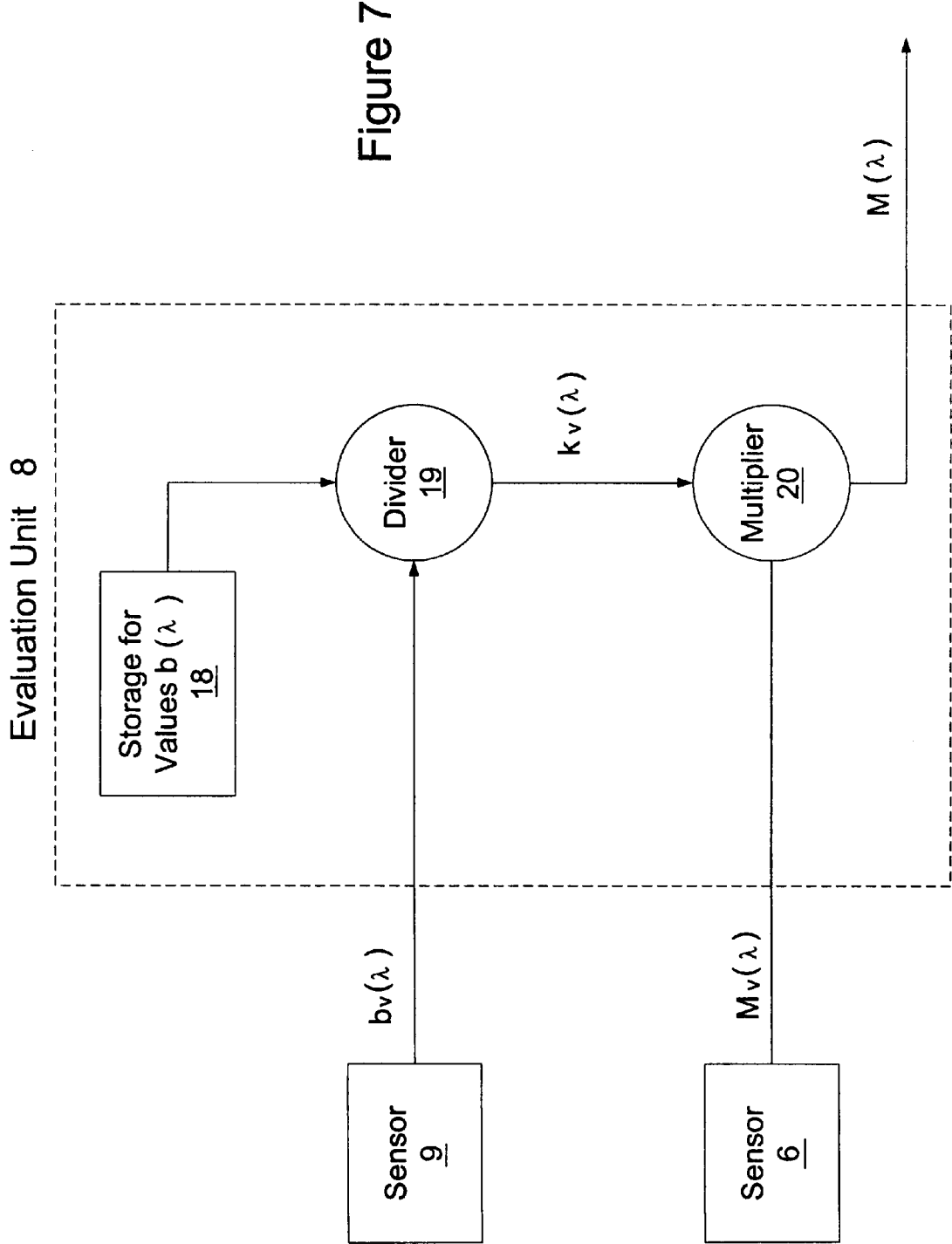

METHOD AND DEVICE FOR DETECTING SPECTRAL REFLECTANCE

FIELD OF THE INVENTION

The invention relates to a method and a device for detecting spectral reflectance.

BACKGROUND OF THE INVENTION

In printing machines, particularly in sheet-fed offset printing machines, it is necessary, for purposes of quality control, to detect actual reflectance values by means of measuring devices preferably located inside the machine, and to derive therefrom quality data, or manipulate variables for process control. Particular use is made of densitometers/spectral densitometers, color-measuring instruments and so-called "spectrophotometers". With these "spectrophotometers", it is advantageous that the light, of a measuring point can be analyzed spectrally by means of these measuring instruments, and can be analyzed with respect to various criteria by further digital processing. Thus, for example, it is possible by means of digital weighting, to use the spectral reflectance of a measuring point to derive both the color density values which have long been used in printing technology, and colorimetric parameters in accordance with the spectral distribution curves of the CIE standard observer. The measured reflectance values described above (densitometric, colorimetric, and spectral) can be obtained both on measuring fields, which have been specially configured and expressly printed in the same forms, and at measuring points which can be arbitrarily selected on the subject (the actual image). The latter has the advantage that there is no need for additional space on the printing carrier and that, furthermore, the quality and process control data are derived directly from the actual printed product.

In the case of measuring devices which are used, in particular, to obtain spectral reflectance data directly inside the running machine, it is necessary to adapt the sensor sensitivity, the illuminance, and the measuring field size to one another. Specifically, in the case of rapidly running printing machines, for a given measuring field size (millimeter range) and a maximum achievable illuminance, only certain specific measuring times are available within which the sensor system, specifically of a spectral reflectance measuring instrument, has to convert the received light quantity. This means that the measuring spot geometry is a function of the aperture restrictor geometry, the relative speed between the printing carrier and the measuring field, the measuring instrument, and the integration time of the sensor(s). The effects of a change in the relative speed of the printing carrier and therefore the measuring field relative to the measuring instrument (printing speed) can be minimized within given limits by varying the integration time of the sensor system. However, this does not cover the entire range of print speed. In order to utilize fully the dynamic range of the sensor system, and thus to also achieve the selected accuracy, it is further necessary to change the illuminance. In the case of high print speeds, more light will have to be applied to a measuring field of prescribed size than in the case of lower print speeds.

EF 0 373 283 B1 discloses a measuring device for inspecting the quality of a printing carrier, where a neutral density filter, with a continuously changing optical density of transmission, is moved in the illuminating-beam path of the measuring field illumination as a function of the printing speed. The movement is accomplished by a remotely controlled drive, which obtains its signals from the controller. The controller is connected to a sensor system which detects the speed of the printing machine. As a result, this measuring device can be used to always scan measuring fields of given size in the optimum region of sensor sensitivity where the illuminating device has a constant control and the print speed varies. However, having a moveable neutral density filter with a controller is disadvantageous because of additional moving parts, sensitivity to mechanical disturbing influences, and exposure to possible contamination.

For the purpose of adapting a plurality of illuminating sources to the same color temperature, it is known from Wo 95/00335 A1 that it is possible to calibrate measurements to a calibration standard (white standard). In this process, the color temperature of the illuminating device of the respective measuring device, or a measure, reproducing the color temperature of the spectral energy distribution of the illuminating device is processed with the aid of the measured photometric variables. This procedure and devices are likewise used inside a printing press where the printing carrier has a relative speed with respect to the measuring device.

An illuminating device for a color measuring instrument in which additional measuring transducers are provided for detecting the radiation produced by a halogen lamp is known from DE 40 13 422 A1. The signals from the transducers are used to achieve a desired color temperature of the illuminating radiation by varying the lamp voltage.

SUMMARY OF THE INVENTION

It is therefore the object of the present invention to develop a method and a corresponding device that improves the optical reflectance measuring system for different print speeds, given a prescribed measuring field size, while avoiding the above mentioned disadvantages.

In accordance with the invention it is provided, in general, that: 1) a variable directly influencing the illuminances/level of illumination of the light source is varied as a function of the relative speed of the printing carrier and measuring field to the measuring device in such a way that a higher illuminances/level of illumination are generated for higher relative speeds, 2) the spectral energy distribution is determined, and 3) during the evaluation this determined spectral energy distribution of the illuminating light is also processed for the illuminance/level of illumination present, in conjunction with the light reflected by the measuring point and received in the photoelectric transducer, in such a way as to calculate the different spectral energy distributions of the illuminating light which result for different illuminances/level of illumination.

The present invention can be realized through a number of variations. It is possible to vary the voltage and/or the current of the illuminating device (at least one incandescent lamp) as a function of the print speed (either continuously or within specific printing speed ranges in a stepped fashion); or individually operate a plurality of incandescent lamps, particularly of different power, in a prescribed manner. By coupling out light from the illuminating device (for example semitransparent mirror or diaphragm mirror), a portion of the radiation of the illuminating device is diverted onto a special reference measuring sensor system by means of which the spectral intensity distribution of the radiation produced by the illuminating device is detected in two or more spectral regions. It is sufficient that the reference sensor system analyzes the radiation from the illuminating device in three spectral regions, for example. The spectral energy distribution is then interpolated via the interpolation points. The illumination spectrum/spectral energy distribution of the illuminating device thus determined is then taken into account when evaluating the light reflected by the actual measuring point in such a way that the different spectral energy distributions occurring for different illuminances are converted to a uniform illuminance and a given spectral energy distribution (for example standard illuminate).

A second method uses a white standard in the form of a test plate (for example barium sulfate) arranged in the outcoupling beam path for the purpose of determining the spectral energy distribution of the illuminating device as a reference measurement. With this method, a white reference measurement is carried out simultaneously with the detection of the spectral reflectance of the measuring field, with changes in the spectral intensity of the illuminating light being taken into account. After appropriate photoelectric conversion by the measuring system, the light reflected by the measuring field is calculated. The measured values and spectral energy distribution obtained correspond to an illuminance which is always constant. Such measurement in conjunction with a white standard (for example barium sulfate) is particularly sensible when detecting colorimetric measured values or spectral measured values for further colorimetric processing.

The device used to measure the spectral intensity distribution of the illuminating source can be the same spectral measuring system as is used to measure the radiation reflected by the measuring field. In particular, a CCD line or planar sensor, which has been extended to form a spectral measuring system, together with an appropriate optical series element (for example a diffraction grating) can be used. As an alternative, it is also possible to use a coarsely revolving spectral measuring system, for example a sensor system which analyzes and quantitatively evaluates the illuminating radiation in a red, in a green and in a blue region, to determine the distribution of the illuminating light. In the case of such an analyzing system, the result for the entire spectrum of the illuminating device is the total of the three measured values, from which it is then possible to determine the spectral energy distribution of the illuminating device through computation by interpolating, on the basis of the algorithms, which take account of the spectral characteristics of the illuminating device. As before, the spectral intensity distribution of the illuminating device, determined by means of specific algorithms, is used in conjunction with the sensor system detecting the reflected light of the measuring field to calculate the measured values with respect to a fixed illumination value (standardization).

The two cases outlined above rely on the finding that the spectral energy distribution, by wavelength, of the light produced by an illuminating device, and reflected by a measuring field, can be represented mathematically as the product of the illuminating spectrum and the spectral reflection (reflectance characteristic/diffuse reflectance) of the reflecting area or of the measuring area (printing carrier plus printing ink application). Using $b(\lambda)$ to denote the spectral intensity distribution of the illuminating light, $r(\lambda)$ to denote the spectral reflectance of the measuring field, and $M(\lambda)$ to denote the spectral intensity distribution of the light reflected by the measuring field and received by the measuring system, the finding states that $M(\lambda)=r(\lambda) \cdot b(\lambda)$.

If, in the case of different printing or relative speeds v, a different $b_v(\lambda)$ is used by appropriately controlling the illuminating device of the measuring system, then different spectral intensity distributions of the light $M_v(\lambda)$ received by the measuring system will result for different relative speeds v. Therefore, $M_v(\lambda)=r(\lambda) \cdot b_v(\lambda)$. This formula assumes that the spectral reflectance $r(\lambda)$ of the measuring area is independent of the illuminance and of the spectral intensity distribution of the illuminating light. This assumption applied with adequate accuracy for the printing inks/printing carriers normally used.

In accordance with the relationship shown above, the spectral energy distribution $b_v(\lambda)$ of the illuminating light is a function of the print or relative speed v. For different illuminances, and thus different spectral compositions of the illuminating light $b_v(\lambda)$, different measuring spectra $M_v(\lambda)$ and different evaluations of the measuring light (calorimetric or densitometric) will result. In order to arrive at an evaluation of the measuring light $M(\lambda)$ reflected by the measuring field, which is independent of the relative speed v, it is necessary only to carry out the following conversion: $M(\lambda)=r(\lambda) \cdot b_v(\lambda) \cdot b(\lambda)/b_v(\lambda)$. Setting $k_v(\lambda)=b(\lambda)/b_v(\lambda)$ yields: $M(\lambda)=r(\lambda) \cdot b_v(\lambda) \cdot k_v(\lambda)$. Thus, despite different intensities of illumination or spectra $b_v(\lambda)$, in the case of different relative speeds v, a spectrum the light $M(\lambda)$ reflected by the measuring field is obtained by using a speed-dependent correcting quantity $k_v(\lambda)$, containing an intensity-distribution $b_v(\lambda)$ of the illuminating light which is a function of the current relative speed v. $M_v(\lambda)$ and $b_v(\lambda)$ are detected at each measurement. Thus, the correcting quantity $k_v(\lambda)$ can be determined with the aid of a stored spectrum $b(\lambda)$ and consequently the measured spectrum $M(\lambda)$ referenced to a standard type of illumination can be determined: $M(\lambda)=M_v(\lambda) \cdot k_v(\lambda)$.

These and other objects and advantages of the invention will become apparent to those skilled in the art from the following detailed description of the preferred embodiment, especially when considered in connection with the accompanying claims and drawings, wherein like numerals refer to like elements.

BRIEF DESCRIPTION OF THE DRAWINGS

FIG. 7 is a block diagram of the evaluation unit in FIGS. 1–4.

DETAILED DESCRIPTION OF THE PREFERRED EMBODIMENT

Figure 1:
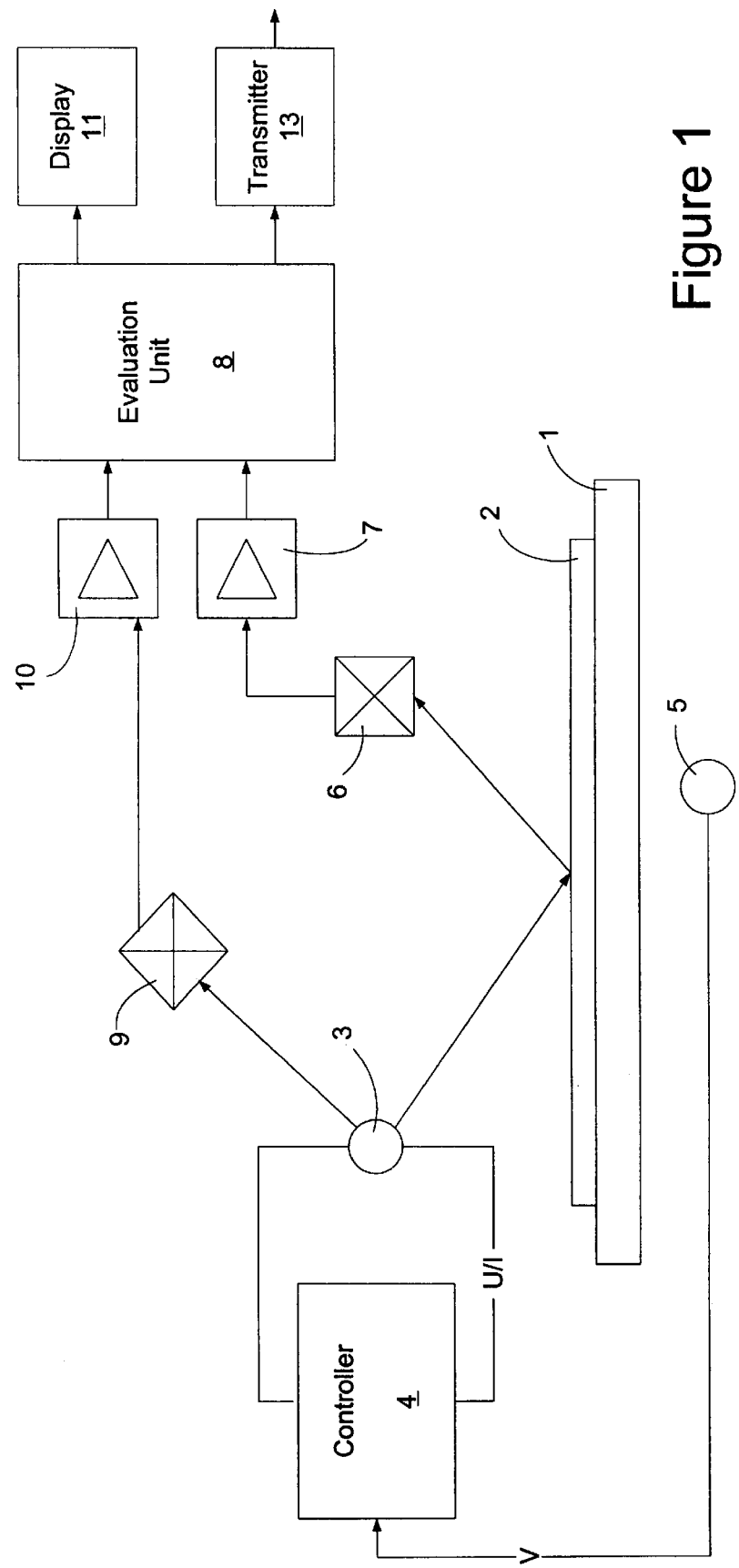
FIG. 1 illustrates one preferred embodiment using only one lamp, and no white standard.
Figure 5:
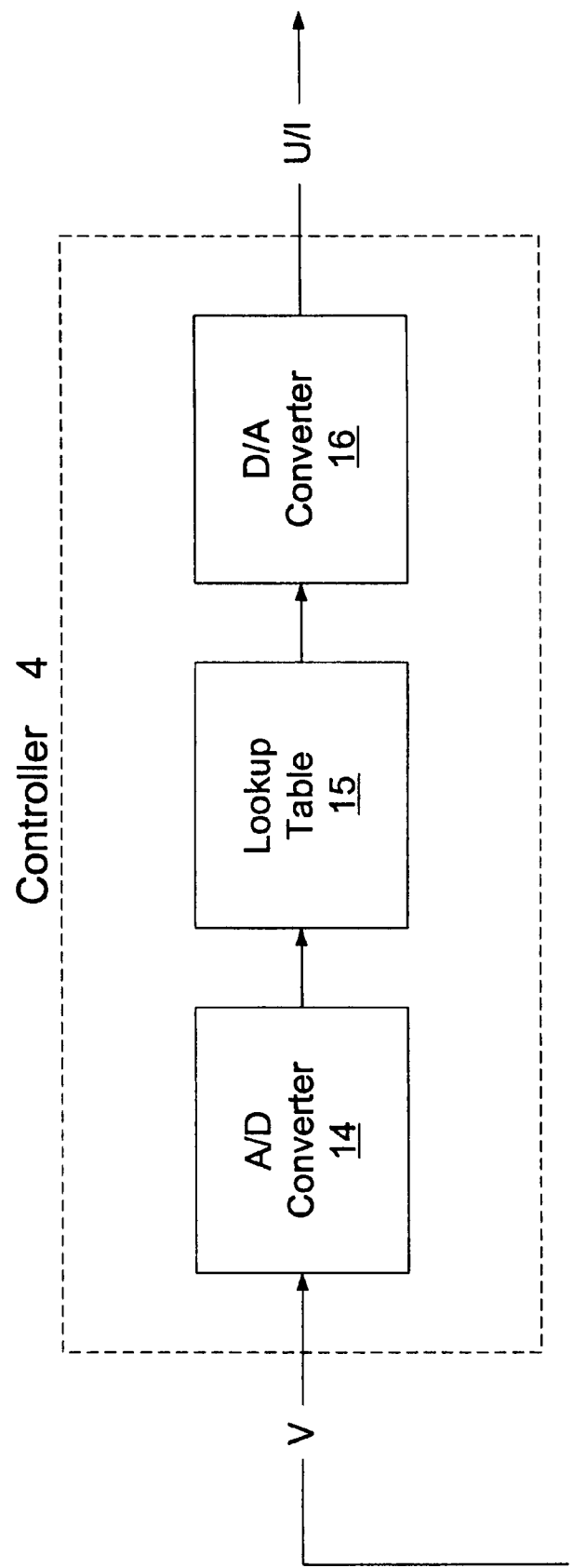
FIG. 5 is a block diagram of the controller 4 in FIGS. 1 and 2.
Figure 6:
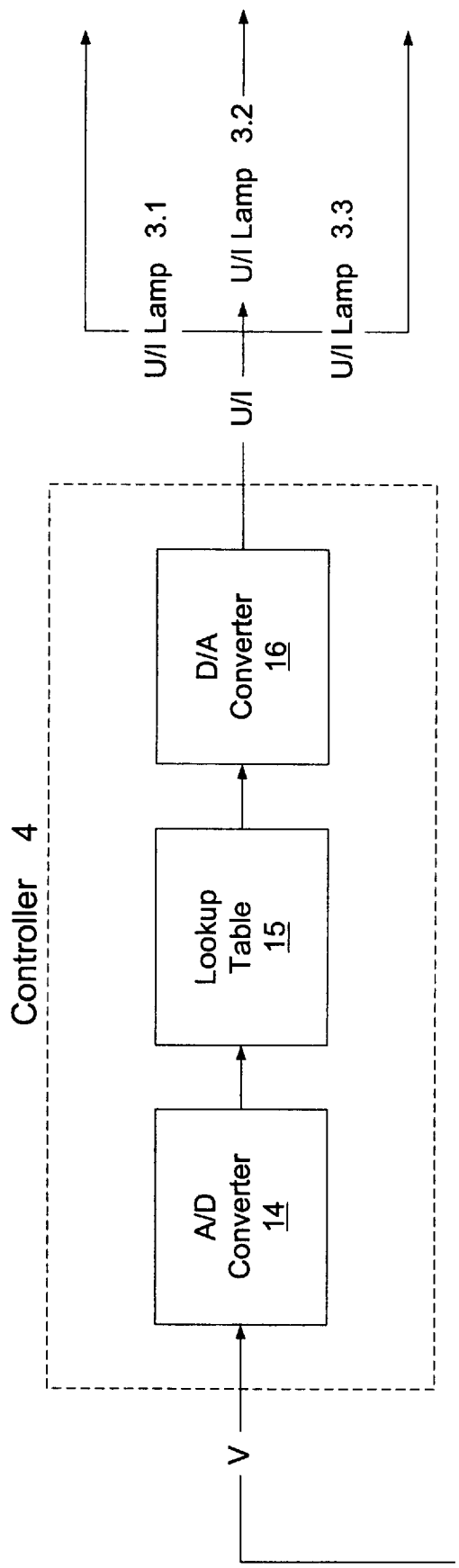
FIG. 6 is a block diagram of the controller 4 in FIGS. 3 and 4.

Exemplary embodiments of the invention are explained with the aid of the drawings. FIGS. 1–4 illustrate possible implementations of the invention, FIGS. 5 and 6 illustrate exemplary implementations of the controller 4 from FIGS. 1–4, and FIG. 7 illustrates a exemplary implementation of the evaluation unit 8 from FIGS. 1–4. A measuring field 2 of a given size, which moves at the speed v relative to the measuring system indicated in FIG. 1 is located on a printing carrier 1 and is irradiated via an illuminating optical system (not represented) by an illuminating device designed as an incandescent lamp 3. The incandescent lamp 3 of the illuminating device is operated in a thin case via an assigned controller 4 by means of the operating voltage U provided and the corresponding operating current I. The controller 4 of the lamp 3 of the illuminating device is connected by signal to a transducing sensor 5 which detects the printing speed v.

The controller 4 is preferably a programmable controller because, for the purpose of operating the lamp 3, the speed ranges of the relative speed v, which are to be determined in tabular form, and values of the operating voltage U and the current I, which are provided in the form of a stored functional relationship of different values of the relative speed v, should be stored in the lookup table 15 of controller 4. As shown in FIG. 5, the speed is converted to a digital value by the A/D converter 14 of controller 4. The appropriate value of the operation voltage U, and corresponding current I, is then determined from the lookup table 15, implemented through a digital storage device such as random access memory or a hard drive, and is sent to the lamp 3 by the D/A converter 16 of controller 4. Consequently, the lamp 3 is controlled to irradiate the measuring field 2 differently in the case of different relative speeds v; that is, the illuminance/level of illumination varies as a function of the relative speed v.

The light of the lamp 3, reflected by the measuring field 2, moving at speed v relative to the measuring system on the printing carrier 1, is projected onto a photoelectric receiver 6 by optical means (diaphragms, lenses, optical fibers, etc., not represented). The photoelectric receiver 6 can, in this case, be a spectral receiver which selectively evaluates the light in different wavelengths and converts it into correspondingly interrogatable signals. The preferred implementation is a CCD line sensor or a diode line having an upstream spectral analyzer (a grating, for example). Such photoelectric receivers 6, and spectral reflectance receivers are known, and therefore require no further explanation. The signals of the photoelectric receivers 6 are amplified via an amplifier 7 and are relayed to a downstream evaluation unit 8.

The evaluation unit, shown in FIG. 7, consists of a digital storage device 18 for values of $b(\lambda)$, implemented as random access memory or a hard drive. Those values are sent to a digital processing unit 19, preferably a digital signal processing CPU or a math-coprocessor, where they are divided by the values from sensor 9. This result is sent to another digital processing unit 20, again preferably a DSP or a math-coprocessor, where it is multiplied to the values from sensor 6. This result is then the speed-independent spectral reflectance measurement.

In addition to photoelectric receiver 6 which detects the light reflected by measuring field 2, there is also a photoelectric receiver 9, which directly detects the radiation from lamp 3, as well an optical means (not represented) which performs spectral analysis of the light directly emitted from the lamp 3. Photoelectric receiver 9 can be a CCD line sensor or a diode line which is extended to form a spectral analyzing system by a series connection of, for example, a diffraction grating. Photoelectric receiver 9 is connected to the input side of amplifier 11 whose output signal is fed to the evaluation device 8. The evaluation, explained above, of the spectral intensity distribution of the light $M_v(\lambda)$ reflected by the measuring field and the light $b_v(\lambda)$ omitted directly from the lamp 3 (according to the relative speed v), is performed in the evaluation device 8. The evaluation device 8 calculates a measured value $M(\lambda)$, which is referenced to a stored illuminance (spectral intensity distribution $b(\lambda)$) and can be represented on display device 11 on the output side of the evaluation device 8. The measured value $M(\lambda)$ can also be fed via a transmitter 13 to a further-processing station (not represented) in which appropriate data can be formed for quality control, derivation of controlled variables, etc.

Figure 2:
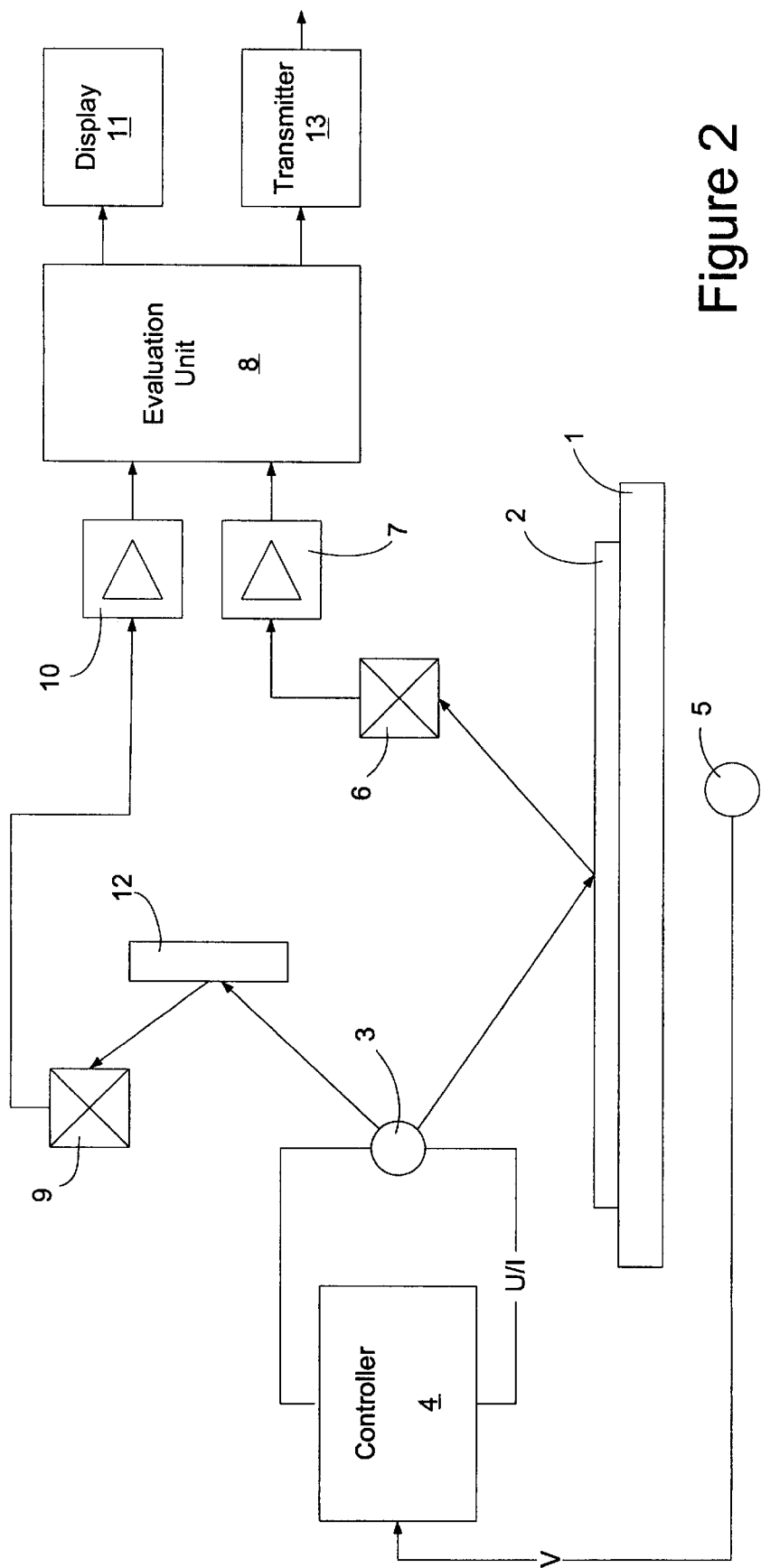
FIG. 2 illustrates another preferred embodiment where only one lamp is used, but a white standard used.

The measuring device represented in FIG. 2 differs from the variant shown in FIG. 1 because there is arranged, in the beam path for illuminating photoelectric receiver 9 by light emitted directly from lamp 3, in accordance with the printing speed v, a white standard 12 (absolute white) which reflects the light from the lamp 3. As in the previous example, the output signals of the photoelectric receiver 9 are fed via amplifier 10 to the evaluation unit 8, which processes the inputs from photoelectric receivers 6 and 9 in the manner described above. Similarly, the evaluation unit 8 calculates a measured value $M(\lambda)$ which is independent of the different spectral intensity distributions of the lamp 3 (and thus of the printing speed) and which can be represented on display device 11 or can be relayed via transmitter 13.

It has already been indicated above that photoelectric receiver 9, which detects the light emitted directly from the lamp 3, can be designed the same way as the receiver used for spectral division and photoelectric conversion of the light reflected by the measuring area 2. It is also possible to design photoelectric receiver 9 as a sensor system which selectively detects the light from the lamp 3 in, for example, two or three different spectral regions, and to use the measured values obtained to determine the spectral intensity distribution of the light on the basis of interpolation algorithms. This can be done simply for the light from incandescent lamps, which has a continuous spectrum.

Figure 3:
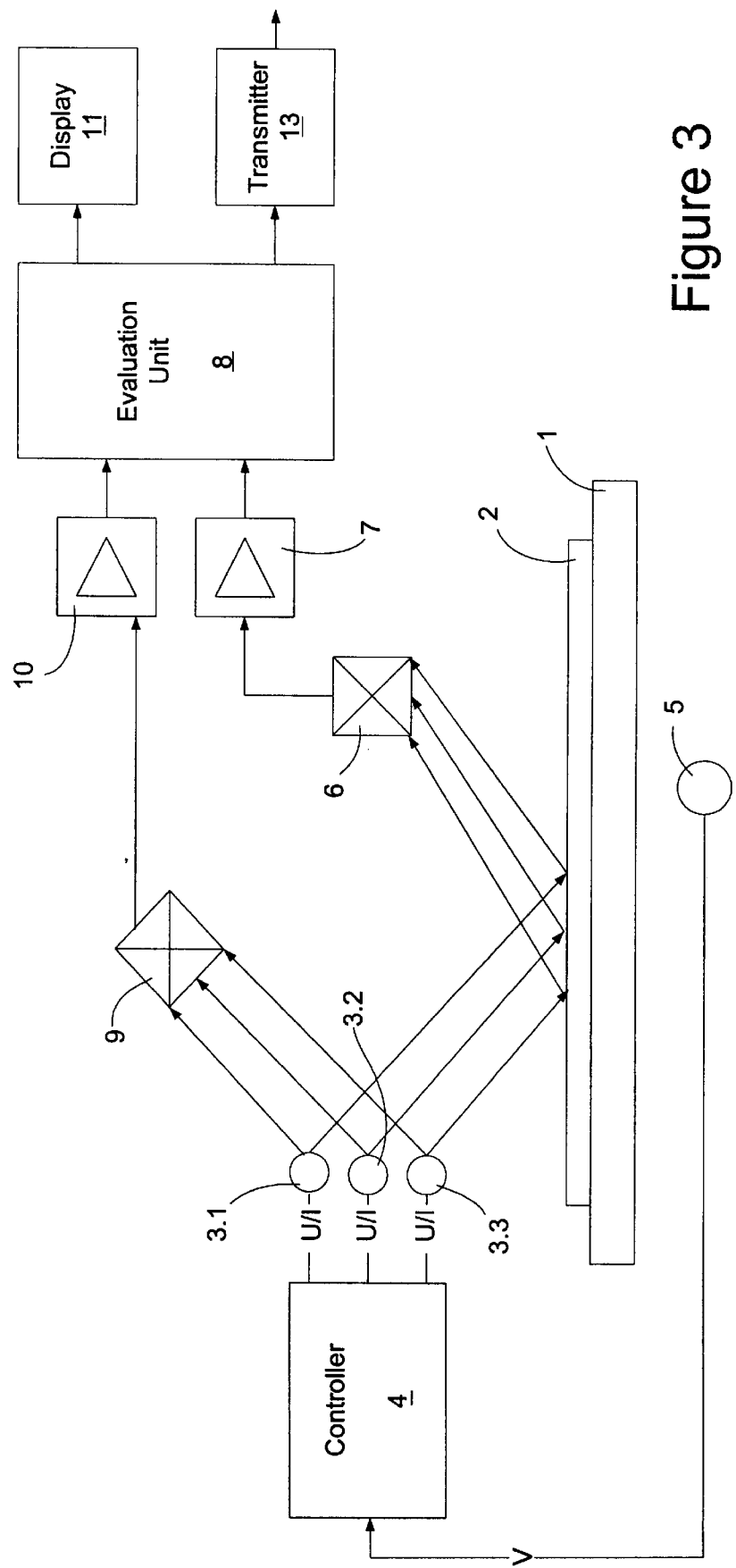
FIG. 3 illustrates another preferred embodiment where multiple lamps are used, though no white standard is used.
Figure 4:
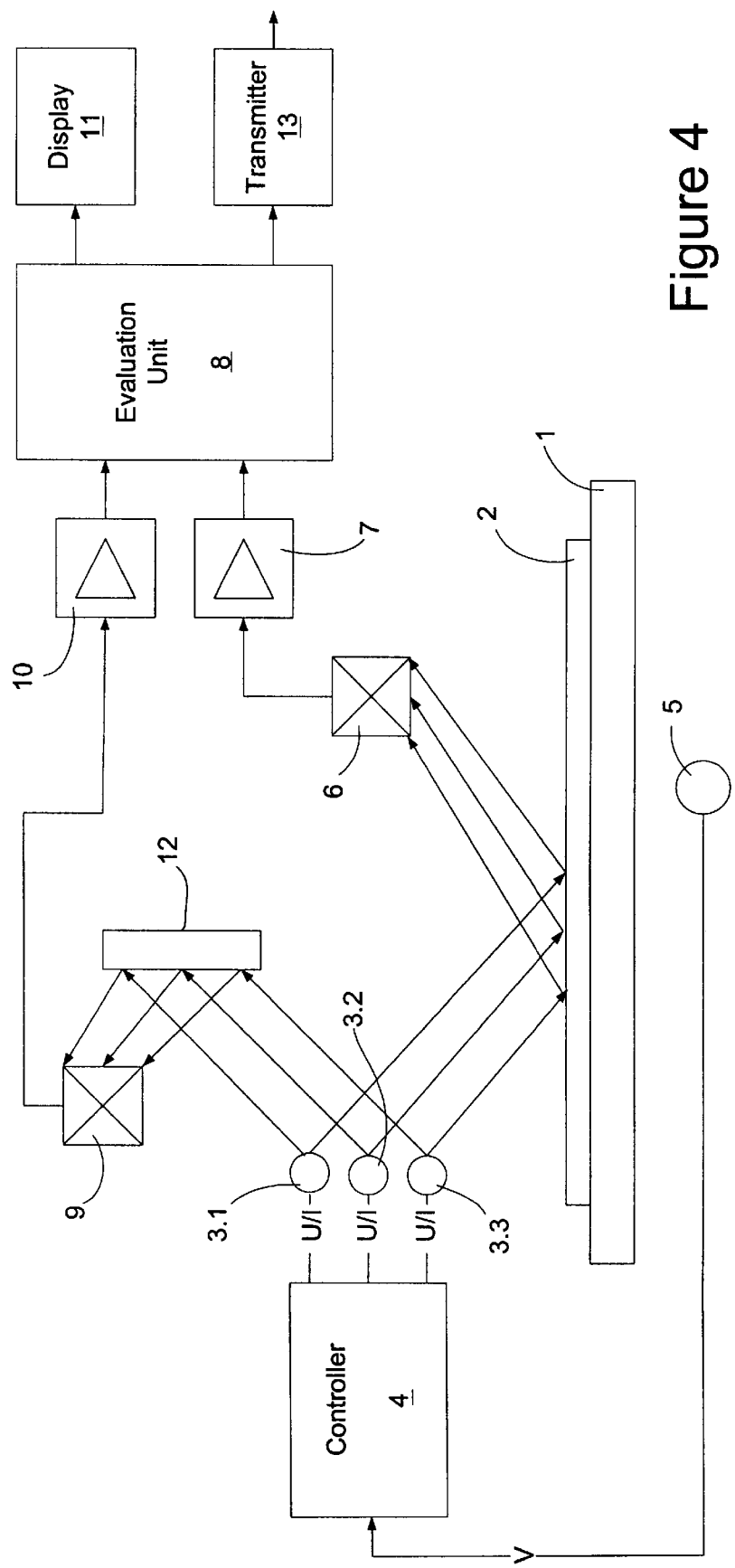
FIG. 4 illustrates another preferred embodiment, in this case multiple lamps are used as is a white standard.

In the embodiments shown in FIGS. 3 and 4, the illuminating device has a total of three lamps 3.1, 3.2, and 3.3 which can be controlled individually by controller 4. As shown in FIG. 6, the controller 4 is identical to the controller 4 from FIG. 5 (the one lamp configuration) except that a lamp driver 17 is used as the output device. The lamp driver 17 is used to control lamps, 3.1, 3.2, and 3.3, which are of different power and are tuned to one another. It is preferable for lamp 3.2 to have double the power of lamp 3.1, and lamp 3.3 to have double the power of lamp 3.2. It is possible, by controlling one or more of lamps 3.1, 3.2, and 3.3, individually or in combination, to emulate an illuminating device which has a power range corresponding to seven times the power of lamp 3.1. It is also possible to control at least one of the lamps, 3.1, 3.2, or 3.3, continuously or in power stages, at least in a portion of the power range, so as to produce a continuous or quasi-continuous adaptation of the illuminating power in accordance with the respective relative speed v.

This invention has been described herein in considerable detail in order to comply with the Patent Statutes and to provide those skilled in the art with the information needed to apply the novel principles and to construct and use such specialized components as are required. However it is to be understood that the invention can be carried out be specifically different equipment and devices, and that various modifications, both as to the equipment details and operating procedures, can be accomplished without departing from the scope of the invention itself.

What is claimed is:

1. A method for detecting spectral reflectance comprising: illuminating a measuring field with an illuminating device, arranged in a stationary fashion; processing a radiation reflected by the measuring field, after photoelectric conversion, to derive measured variables; varying an intensity of the illuminating device as a function of a relative speed between the measuring field and a measuring system, in that a spectral intensity distribution of a light source of the illuminating device is detected for a respective relative speed between the measuring field and the measuring system; accounting for the spectral intensity distribution of the light source of the illuminating device in processing the radiation reflected by the measuring field to obtain measured values; detecting the intensities in at least two spectral regions; and interpolating via at least two detected spectral intensities as interpolation points in order to determine the spectral intensity distribution of the radiation of the illuminating device.

2. A measuring device comprising: an illuminating device for irradiating measuring fields, moving with respect to the measuring device, on a printing carrier; a control device inside the illuminating device for varying an irradiance of the measuring fields as a function of a relative speed between the measuring fields and the measuring device; at least one measuring channel for photoelectric conversion of a radiation reflected by the measuring fields and; a downstream evaluation unit for determining measured values of the radiation reflected by the measuring fields, in which a photoelectric transducer in the measuring channel assigned to the light source, and a photoelectric transducer in the measuring channel assigned to the measuring field, are designed as measuring systems of the same kind.

3. A method for determining spectral reflectance comprising: irradiating a measuring field by a radiation source; varying an intensity of a radiation from the radiation source based on a relative speed between the measuring field and the radiation source; detecting a spectral intensity distribution of a reflected radiation from the measuring field; detecting a spectral intensity distribution of the radiation from the radiation source, and; dividing the spectral intensity distribution of the radiation from the radiation source by a stored, reference spectral intensity distribution and then multiplying by the spectral intensity distribution of the reflected radiation from the measuring field to determine a speed-independent spectral reflectance.

4. The method of claim 3, including the step of irradiating the measuring field with one radiation source, and varying the voltage and corresponding current to vary the intensity of the radiation source.

5. The method of claim 3, including the step of irradiating the measuring field with multiple radiation sources, and turning on the multiple radiation sources in combinations to vary the intensity of the radiation source.

6. The method of claim 4, including the step of detecting the spectral intensity distribution of the radiation from the radiation source by detecting a spectral intensity distribution of a reflected radiation from a white standard.

7. The method of claim 6, including the step of detecting the spectral intensity distribution of the radiation from the radiation source by detecting a spectral intensity distribution of a reflected radiation from a white standard.

8. A method for detecting spectral reflectance comprising: illuminating a measuring field with an illuminating device arranged in a stationary fashion; processing a radiation reflected by the measuring field after photoelectric conversion to derive measured variables; varying an intensity of the illuminating device as a function of a relative speed v between the measuring field and a measuring system, in that a spectral intensity distribution of a light source of the illuminating device is detected for a respective relative speed v between the measuring field and the measuring system; accounting for the spectral intensity distribution of the light source of the illuminating device in processing the radiation reflected by the measuring field to obtain measured values; and turning on and off in different combinations a plurality of light sources in the illuminating device as a function of the relative speed v.

9. A measuring device comprising: an illuminating device for irradiating a measuring field moving with respect to the measuring device on a printing carrier; a control device inside the illuminating device for varying an irradiance of the measuring fields as a function of the relative speed between the measuring field and the measuring device; at least one measuring channel for photoelectric conversion of a radiation reflected by the measuring field and; a downstream evaluation unit for determining measured values of the radiation reflected by the measuring field, in which the radiation of the light source can be detected in at least two spectral regions by a photoelectric transducer in the measuring channel assigned to the light source, with an evaluation unit which interpolates via the detected spectral intensities as interpolation points.

10. A measuring device comprising: an illuminating device for irradiating a measuring field moving with respect to the measuring device on a printing carrier; a control device inside the illuminating device for varying an irradiance of the measuring field as a function of the relative speed between the measuring field and the measuring device; at least one measuring channel for photoelectric conversion of a radiation reflected by the measuring field and; a downstream evaluation unit for determining measured values of the radiation reflected by the measuring field, in which the illuminating device has a plurality of light sources, which are designed as incandescent lamps, and can be turned on or off in combinations via the controller as a function of the relative speed between the measuring field and the measuring device.

* * * * *